(12) United States Patent
Wang et al.

(10) Patent No.: US 10,451,573 B2
(45) Date of Patent: Oct. 22, 2019

(54) METHOD AND SYSTEM FOR GAS TEMPERATURE MEASUREMENT

(71) Applicant: General Electric Company, Schenectady, NY (US)

(72) Inventors: Guanghua Wang, Clifton Park, NY (US); Danielle Marie Kalitan, Rexford, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 99 days.

(21) Appl. No.: 15/077,663

(22) Filed: Mar. 22, 2016

(65) Prior Publication Data

US 2017/0276622 A1 Sep. 28, 2017

(51) Int. Cl.
*G01N 25/00* (2006.01)
*G01K 7/02* (2006.01)

(52) U.S. Cl.
CPC .............. *G01N 25/00* (2013.01); *G01K 7/02* (2013.01)

(58) Field of Classification Search
CPC ................................. G01K 7/02; G01N 25/00
USPC ........................................................ 73/25.01
See application file for complete search history.

(56) References Cited

U.S. PATENT DOCUMENTS

| 3,935,032 | A | 1/1976 | Brandeberry et al. |
| 4,038,105 | A | 7/1977 | Brandeberry et al. |
| 4,187,434 | A | 2/1980 | Pater, Jr. et al. |
| 4,525,080 | A | 6/1985 | Smith |
| 5,112,215 | A * | 5/1992 | Frish ................. F23N 5/003 236/15 E |
| 5,116,137 | A | 5/1992 | Xiong et al. |
| 7,754,491 | B2 * | 7/2010 | Park ................... G01N 27/18 422/78 |
| 2011/0299562 | A1 * | 12/2011 | Hashemian .......... G01K 7/18 374/1 |
| 2012/0247108 | A1 * | 10/2012 | Romig ............... G01N 1/2252 60/722 |
| 2014/0033737 | A1 * | 2/2014 | Wang ................ F01D 17/085 60/803 |
| 2015/0049786 | A1 * | 2/2015 | Wang ................ G01M 15/14 374/138 |

FOREIGN PATENT DOCUMENTS

| GB | 890490 A | 2/1962 |
| WO | 8904951 A1 | 6/1989 |

OTHER PUBLICATIONS

Sullivan Patrick, "Kiln Interior Temperature Transducer", Industry and General Applications, IEEE Transactions on, vol. IGA-6, Issue: 5, pp. 503-508, Sep. 1970.

(Continued)

*Primary Examiner* — Justin Seo
*Assistant Examiner* — Jean F Morello
(74) *Attorney, Agent, or Firm* — Christopher R. Carroll; The Small Patent Law Group LLC

(57) ABSTRACT

A multi-function gas temperature measurement probe includes an outer casing, at least one high-temperature thermocouple inserted within the outer casing, at least one gas emissions sampling aperture defined within the outer casing, and at least one thin filament coupled to the outer casing. The at least one high-temperature thermocouple, the at least one gas emissions sampling aperture, and the at least one thin filament are proximate to each other.

20 Claims, 4 Drawing Sheets

(56) References Cited

OTHER PUBLICATIONS

Zhang Zhilin et al., "Multi-wavelength pyrometry for temperature measurement in gas flames", Measurement, Information and Control (MIC), 2012 International Conference on, vol. 1, pp. 198-201, May 18-20, 2012, Harbin.

* cited by examiner

METHOD AND SYSTEM FOR GAS TEMPERATURE MEASUREMENT

BACKGROUND

The field of the disclosure relates generally to gas temperature measurement, and more specifically, to methods and a system for measuring gas temperature in harsh environments using an integrated temperature measurement device including a plurality of temperature measurement techniques.

At least some known turbomachines, such as gas turbine engines, include a plurality of rotating turbine blades or buckets and stationary nozzle segments that channel high-temperature fluids, i.e., combustion gases, through the gas turbine engines. Many of these known gas turbine engines include temperature monitoring systems that provide operational temperature data in real time, i.e., at the time of measurement. Measuring gas temperatures in a combusting flame or harsh environment downstream of a combustor, i.e., a hot gas path may include many sources of inaccuracy and non-repeatability. Many of those relate to physical properties of the temperature measurement mechanisms positioned in or proximate to the flow of the hot combustion gases and/or proximate to the high-temperature gas turbine components. Therefore, to overcome the deficiencies of known temperature measurement mechanisms with respect to gas temperature profiles and near-wall temperature measurements in high-temperature and high-pressure environments, gas turbine manufacturers may elect to fabricate, install, and run hot gas components with greater thermal margins to extend the useful service life of such components. Increasing thermal margins typically manifests as increased wall thicknesses and other ruggedizing methods. Such increased ruggedness of those components increases the costs of production and increases a potential for premature reductions in service life due to excessive temperature profiles induced in the walls of the components during operations that typically include large-scale temperature changes, e.g., startups, shutdowns, and load changes.

Rather than incurring such increased costs associated with increasing the thermal margins high-temperature gas turbine components, manufacturers may choose to install independent and redundant temperature measurement devices that use distinct techniques that include thin filament pyrometry (TFP), high temperature thermocouples, and gas sampling probes. Each technique has characteristics that facilitate accurate and reliable temperature measurements. However, each technique also has at least one drawback. For example, thermocouples and probes for point temperature measurements do not account for radiation effects prominent in the hot gas path. Also, due to the low spatial resolution features and the low accuracy associated with measuring boundary layer temperature profiles, these temperature measurement mechanisms do not provide accurate temperature distribution profiles and alternative computational extrapolations and approximations must be used to facilitate spatial-resolution of the temperature profiles, albeit, with some inaccuracies induced by the modeling techniques and approximations used. In addition, due to the high temperatures in the hot gas path, the service life of the thermocouple wires in such high-temperature environments is shortened. Also, the use of any one of the three techniques identified above eventually requires verification of calibration of the associated temperature measurement devices in harsh test environments to facilitate cross-validation during product testing. As such, redundant temperature measurement devices introduce additional hardware requirements and their associated costs into the instrumentation suite for gas turbine engines.

BRIEF DESCRIPTION

In one embodiment, a multi-function gas temperature measurement probe is provided. The probe includes an outer casing, at least one high-temperature thermocouple inserted within the outer casing, at least one gas emissions sampling aperture defined within the outer casing, and at least one thin filament coupled to the outer casing. The at least one high-temperature thermocouple, the at least one gas emissions sampling aperture, and the at least one thin filament are proximate to each other.

In another embodiment, a gas temperature measurement system is provided. The system includes at least one multi-function gas temperature measurement probe. The probe includes an outer casing, at least one high-temperature thermocouple inserted within the outer casing, at least one gas emissions sampling aperture defined within the outer casing, and at least one thin filament coupled to the outer casing. The at least one high-temperature thermocouple, the at least one gas emissions sampling aperture, and the at least one thin filament are proximate to each other. The system also includes an optical system configured to receive at least a portion of thermal radiation emitted from the at least one thin filament. The system further includes a thermocouple electronics system coupled to the at least one high-temperature thermocouple. The system also includes a gas analyzer system coupled to the at least one gas emissions sampling aperture.

In yet another embodiment, a method of testing at least a portion of a gas turbine engine is provided. The method includes generating thermocouple temperature measurements of at least a portion of a high-temperature combustion gas stream through at least one high-temperature thermocouple of a multi-function gas temperature measurement probe. The method further includes generating thin filament pyrometry (TFP) temperature measurements of the at least a portion of the high-temperature combustion gas stream through at least one thin filament of the multi-function gas temperature measurement probe. The method also includes generating gas species concentration measurements of the at least a portion of the high-temperature combustion gas stream through at least one gas emissions sampling aperture of the multi-function gas temperature measurement probe. The at least one high-temperature thermocouple, the at least one thin filament, and the at least one gas emissions sampling aperture are proximate to each other.

DRAWINGS

These and other features, aspects, and advantages of the present disclosure will become better understood when the following detailed description is read with reference to the accompanying drawings in which like characters represent like parts throughout the drawings, wherein.

Figure 1:
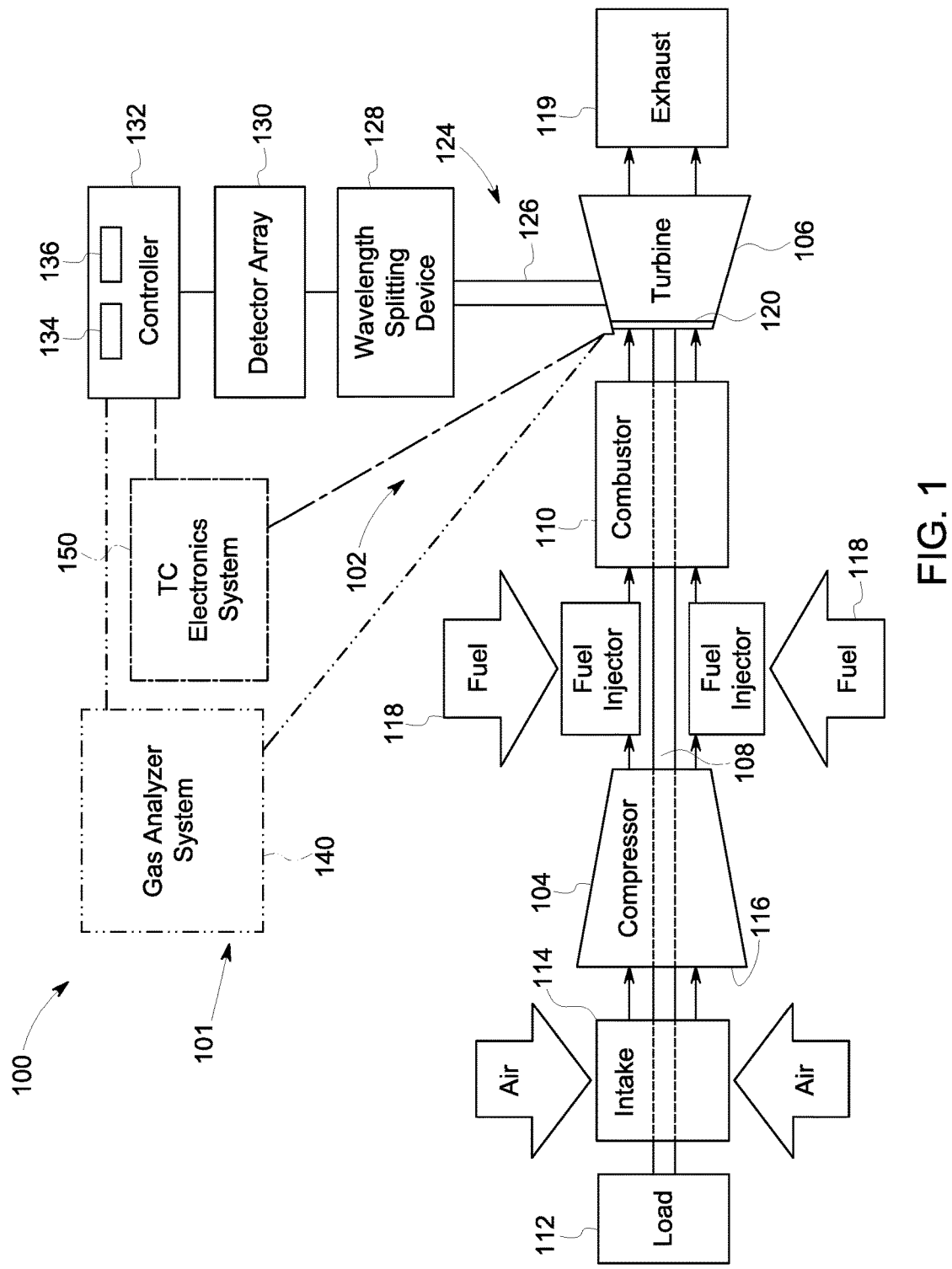
FIG. 1 is a schematic block diagram of an exemplary gas temperature measurement system implemented in an exemplary turbomachine.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that may permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and interchanged; such ranges are identified and include all the sub-ranges contained therein unless context or language indicates otherwise.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

The gas temperature measurement probes and systems described herein use an integrated suite of temperature measurement devices suited for high-temperature environments. Specifically, the gas temperature measurement probes and systems described herein integrate thin filament pyrometry (TFP), high temperature thermocouples (TC), and gas emissions sampling probes into a single package that is easily inserted into the hot gas path of gas turbine engines. Also, the integrated TFP/TC/gas emissions probe is water-cooled to facilitate service life extension in the harsh environments. The TFP portion of the probe facilitates spatial resolution of the temperature fields and gradients in three dimensions and the TFP measurements are compared to the spatially resolved emissions measurements. Moreover, the probes described herein may be used in a stationary mode and they may be mounted on a translating device (or devices) and moved around the hot gas path to get a map of the gas temperatures in several planes. The probes described herein are especially suited for testing arrangements to facilitate cross-validation of the accuracy of gas temperature measurement data for product validation.

FIG. 1 is a schematic view of an industrial facility 100 that includes a turbomachine, and more specifically, a gas turbine engine system 101. In the exemplary embodiment, gas turbine engine system 101 is a land-based gas turbine. Alternatively, gas turbine engine system 101 includes any gas turbine engine that enables operation of system 101 as described herein, including, without limitation, naval gas turbines and aircraft engines. In the exemplary embodiment, gas turbine engine system 101 includes a gas temperature measurement system 102. Gas temperature measurement system 102 may be used in any other facilities and with any other apparatus and processes that use gas temperature measurements, e.g., without limitation, power and auxiliary boilers, other turbomachinery, chemical processing plants, including, without limitation, refining plants, and solar collectors.

In the exemplary embodiment, gas turbine engine system 101 includes a compressor 104 and turbine 106 mounted on a common shaft 108 and coupled in a serial flow arrangement with a combustor 110 positioned between them. A load 112, such as, but not limited to, a generator, a pump, and a compressor is also drivingly coupled to shaft 108.

During operation, air or other oxygen containing working fluid is received at an air intake 114 and directed to an inlet 116 of compressor 104, compressed air is then directed to combustor 110, where fuel 118 is added to the flow of compressed air and ignited, generating a flow of relatively hot, high-energy gases. The gases are directed through turbine 106, where work is extracted to drive compressor 104 and load 112. The exhausted gases are expelled through an exhaust section 119.

While gas turbine engine system 101 is in operation, gas temperature measurement system 102 monitors one or more temperatures of the gases passing through gas turbine engine system 101. Gas temperature measurement system 102 includes a plurality of temperature measurement probes 120 positioned within a flow path of the hot high-energy gases generated in combustor 110. In various embodiments, probes 120 may be positioned at for example, but not limited to, an inlet to combustor 110, an outlet from combustor 110, an inlet to turbine 106, and an outlet from turbine 106. Probes 120 may also be coupled to various components operating in the gas paths of gas turbine engine system 101, such as, but not limited to, stationary surfaces, e.g., compressor vanes, cooling apertures, turbine nozzles, and turbine exhausts, and rotatable surfaces, e.g., land-based turbine buckets, aircraft engine blades, and compressor/fan blades.

Also, in the exemplary embodiment, gas temperature measurement probes 120 are integrated devices that integrate thin filament pyrometry (TFP), high temperature thermocouples (TC), and gas emissions sampling probes into a single package inserted into the associated gas paths. Therefore, for the TFP portions of probe 120, an optical system 124 includes sufficient collection optics, i.e., optical system 124 includes an optical component 126 fabricated of a material that is at least partially transparent to thermal radiation emitted by probes 120 to collect the thermal radiation light from probes 120. Optical component 126 is any device that enables operation of optical system 124 and gas temperature measurement system 102, including, without limitation, windows, lens, and mirrors. Optical system 124 also includes a wavelength splitting device 128 that is configured to split broad wavelength band thermal radiation signals into a plurality of relatively narrow band thermal radiation signals. Optical system 124 further includes at least one detector array 130 that is configured to convert the relatively narrow band thermal radiation signals to digital signals.

In addition, in the exemplary embodiment, gas temperature measurement system 102 includes a controller 132 that includes a processor 134 and a memory 136. Memory 136 includes one or more predetermined algorithms configured, when executed by processor 134 to convert the digital signals into temperature indication based on a predetermined calibration curve. Controller 132 is programmed with sufficient instructions and algorithms to enable operation of gas temperature measurement system 102 as described herein based on measurements collected by the TFP portions of probe 120.

Further, in the exemplary embodiment, gas temperature measurement system 102 includes a gas analyzer system 140 in flow communication with probe 120 and in operative communication with controller 132. Gas analyzer system 140 includes, without limitation, oxygen, carbon monoxide, carbon dioxide, unburned hydrocarbons, methane, and nitrogen oxide measurement devices. Gas analyzer system 140 also includes, without limitation, at least one vacuum pump to facilitate collecting samples from probes 120. Gas temperature measurement system 102 also includes a thermocouple electronics system 150 operatively coupled to probe 120 and controller 132. Thermocouple electronics system 150 includes, without limitation, a reference junction sensor, e.g., without limitation, a semiconductor thermometer, for cold junction compensation. Controller 132 is further programmed with sufficient instructions and algorithms to enable operation of gas temperature measurement system 102 as described herein based on measurements collected by the TC and gas emissions portions of probe 120. In addition, controller 132 is programmed with sufficient instructions and algorithms to enable operation of gas temperature measurement system 102 as described herein to, and without limitation, facilitate spatial resolution of the temperature fields and gradients in three dimensions, compare the TFP measurements with the spatially resolved emissions measurements, and to facilitate cross-validation of the accuracy of gas temperature measurement data for product validation under testing conditions.

As shown in the exemplary embodiment, gas temperature measurement system 102 monitors one or more temperatures of the gases passing through turbine 106 of gas turbine engine system 101. Alternatively, gas temperature measurement system 102 may be used to measure gas temperatures associated with other portions of gas turbine engine system 101, including, without limitation, any portion of air intake 114, compressor 104, combustor 110, and exhaust section 119.

Figure 2:
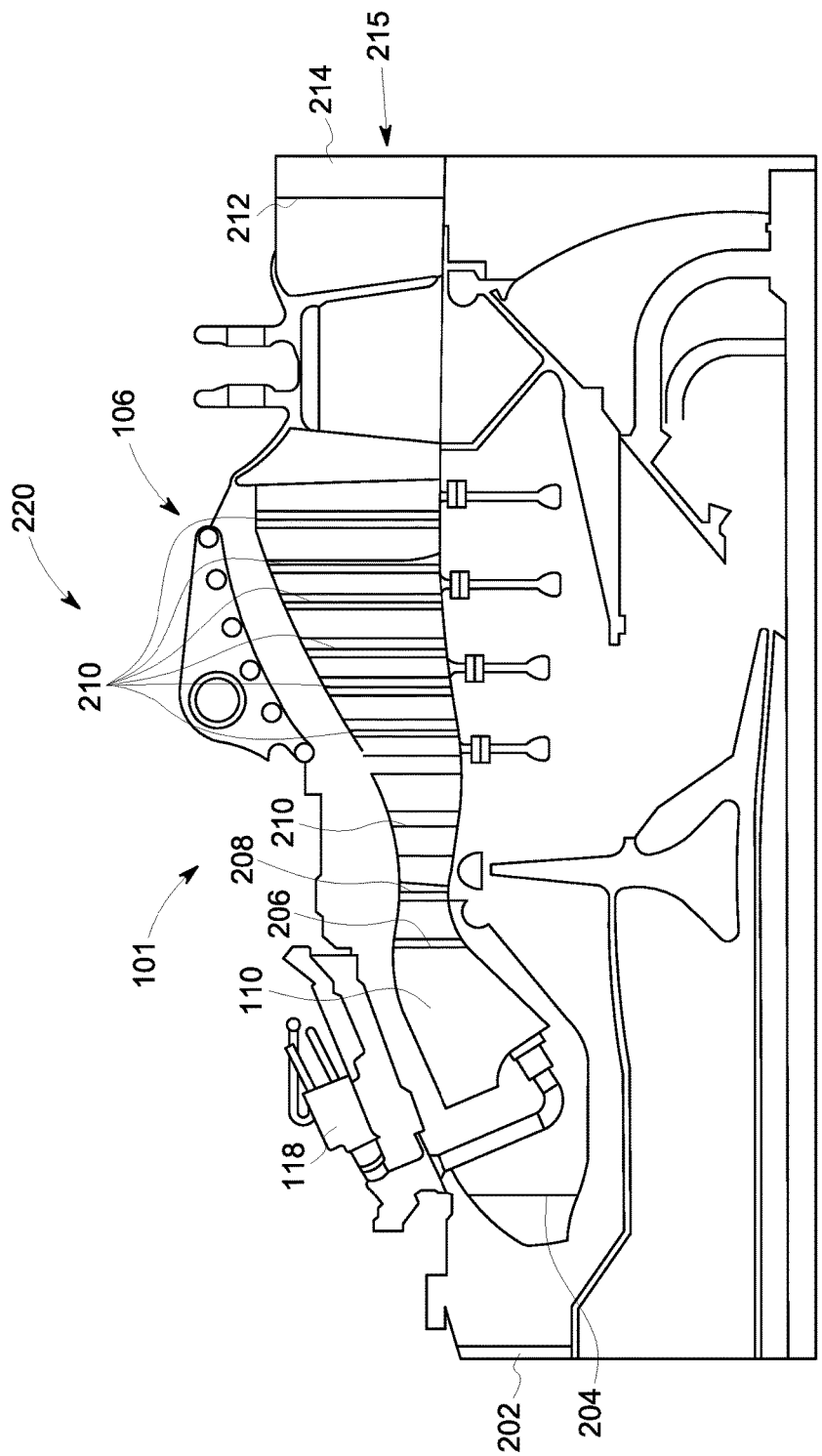
FIG. 2 is a side cross-sectional view of a portion of the turbomachine shown in FIG. 1.

FIG. 2 is a side cross-sectional view of a portion of gas turbine engine system 101. In the exemplary embodiment, FIG. 2 illustrates using gas temperature measurement system 102 to measure gas temperature at a compressor outlet 202, a combustor inlet 204, a combustor exit 206, an S1N location 208, and at inter-stages 210 of turbine 106, and inside or at the exit 212 of one or more nozzles 214 and exhaust 215. In alternative embodiments, gas temperature measurement system 102 can be used to measure gas temperatures in other positions of gas turbine engine system 101 not shown in FIG. 2, e.g., without limitation, air intake 114, compressor 104, exhaust section 119 (all shown in FIG. 1), and secondary flows (not shown) in gas turbine engine system 101. Combustor exit 206, S1N location 208, inter-stages 210, exit 212, nozzles 214, and exhaust 215 define a hot gas path 220.

Figure 3:
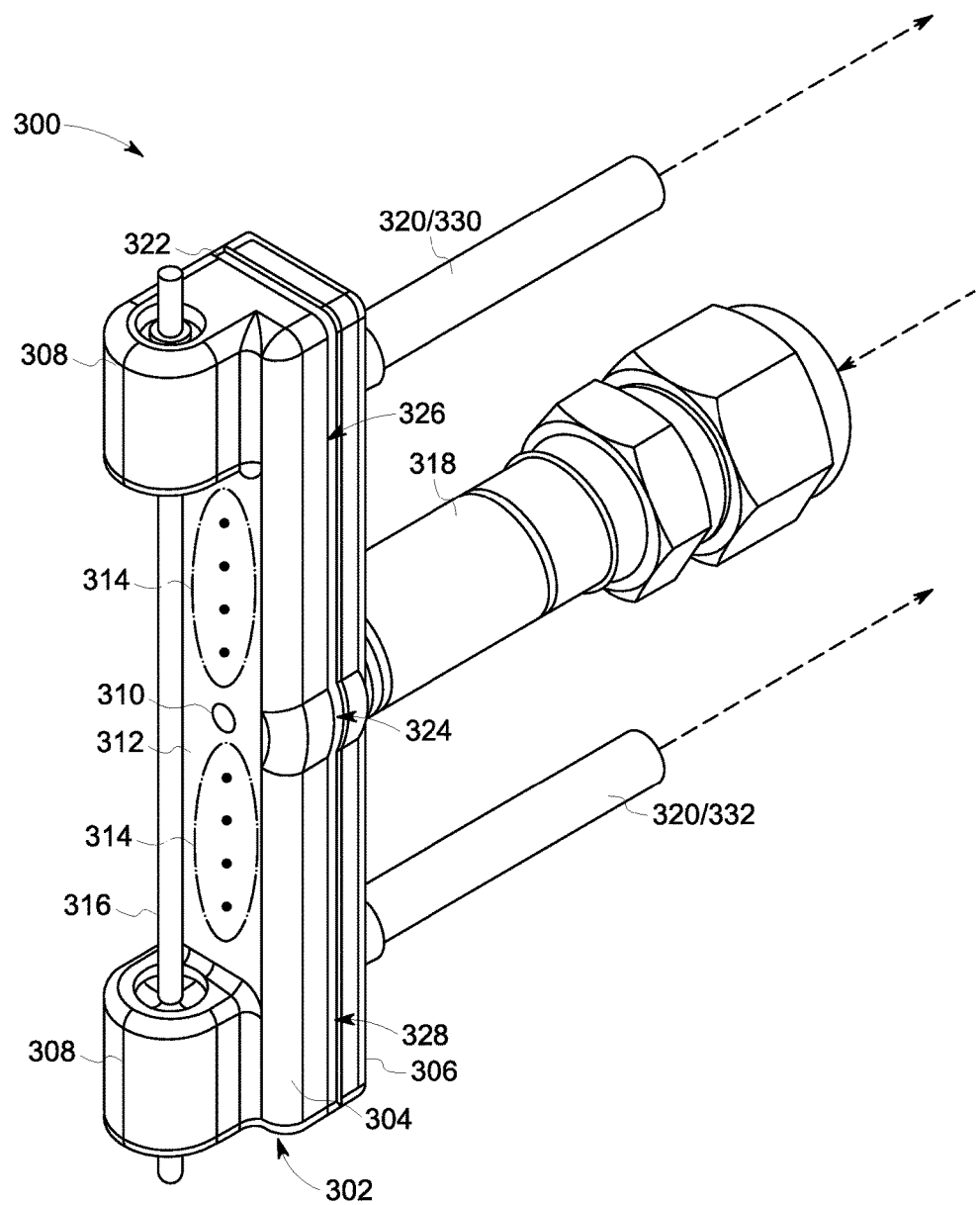
FIG. 3 is a perspective view of an exemplary temperature measurement probe that may be used with the gas temperature measurement system shown in FIG. 1.

FIG. 3 is a perspective view of temperature measurement probe 300 that may be used with gas temperature measurement system 102 (shown in FIG. 1). In the exemplary embodiment, probe 300 is a multi-function gas temperature measurement probe 300 that is substantially similar to each probe of plurality of probes 120 (shown in FIG. 1). Probe 300 includes an outer casing 302 that, in the exemplary embodiment, is fabricated from a high-temperature material, i.e., a high-temperature alloy such as Inconel® 625. Alternatively, outer casing 302 is fabricated from any high-temperature material that enables operation of gas temperature measurement system 102 and temperature measurement probe 300 as described herein, including, without limitation, tungsten alloy, nickel-based alloy, and stainless steel. Outer casing 302 includes a measurement portion 304, a heat removal portion 306, and at least one thin filament standoff 308 (two shown in FIG. 3). In the exemplary embodiment, outer casing 302, including the individual components 304, 306, and 308 is unitarily formed through methods that include, without limitation, additive manufacturing. Alternatively, casing 302 is manufactured through fabricating each of measurement portion 304, heat removal portion 306, and thin filament standoffs 308 using any fabrication process, and coupling measurement portion 304, heat removal portion 306, and thin filament standoffs 308 to form outer casing 302, including, without limitation, welding.

Also, in the exemplary embodiment, multi-function gas temperature measurement probe 300 includes at least one high-temperature thermocouple 310 (only one shown n FIG. 3), inserted within outer casing 302, i.e., inset within a face 312 of measurement portion 304. Alternatively, temperature measurement probe 300 includes any number of high-temperature thermocouples 310 that enables operation of gas temperature measurement system 102 and temperature measurement probe 300 as described herein.

Further, in the exemplary embodiment, multi-function gas temperature measurement probe 300 includes a plurality of gas emissions sampling apertures 314 defined within face 312 of outer casing 302. While eight apertures 314 are shown in FIG. 3, alternatively, temperature measurement probe 300 includes any number of gas emissions sampling apertures 314 that enables operation of gas temperature measurement system 102 and temperature measurement probe 300 as described herein. Apertures 314 are coupled in flow communication with gas analyzer system 140, including, without limitation, vacuum pumps (not shown) through gas transfer conduits (not shown) therebetween.

Moreover, in the exemplary embodiment, multi-function gas temperature measurement probe 300 includes at least one thin filament 316 (only one shown in FIG. 3). Thin filament 316 is removably coupled to thin filament standoffs 308 for substantial securement thereto to facilitate stability of filament 316. As such, standoffs 308 retain and support thin filament 316.

In addition, in the exemplary embodiment, high-temperature thermocouple 310, gas emissions sampling apertures 314, and thin filament 316 are proximate to each other. Such proximate to positioning of such measurement instruments facilitates generating a plurality of measured three-dimensional (3D) temperature fields and a plurality of measured 3D temperature gradients with a predetermined spatial resolution. Also, such proximate to positioning of such measurement instruments facilitates performing a cross-validation of an accuracy of the gas temperature measurement data collected by high-temperature thermocouples 310 and thin filaments 316. Further, such proximate to positioning of such measurement instruments facilitates generating a plurality of measured 3D gas emissions species concentrations with a predetermined spatial resolution. Moreover, such proximate to positioning of such measurement instruments facilitates comparing 3D spatially-resolved temperature field and gradient measurements with spatially-resolved gas emissions species concentration measurements. These cross-correlation features enhance data validation, especially in testing environments.

Multi-function gas temperature measurement probe 300 also includes at least one cooling fluid inlet conduit 318 (only one shown in FIG. 3) and at least one cooling fluid outlet conduit 320 (two shown in FIG. 3). Also, probe 300 includes a cooling fluid shell 322 coupled to, and between, measurement portion 304 and heat removal portion 306. In the exemplary embodiment, cooling fluid shell 322 is fabricated with the remainder of outer casing 302 using additive manufactured or welding as described above. As such, cooling fluid shell 322, measurement portion 304, heat removal portion 306, and thin filament standoffs 308 unitarily form probe 300. Cooling fluid shell 322 defines at least one cooling fluid plenum therein, and in the exemplary embodiment, shell 322 defines a cooling fluid inlet plenum 324, and upper cooling fluid plenum 326, and a lower cooling fluid plenum 328. Cooling fluid inlet plenum 324 is coupled in flow communication with cooling fluid inlet conduit 318. Upper cooling fluid plenum 326 is coupled in flow communication with an upper cooling fluid outlet conduit 330 and lower cooling fluid plenum 328 is coupled in flow communication with a lower cooling fluid outlet conduit 332. While probe 300 is shown with one inlet conduit, one inlet plenum, two outlet plenums, and two outlet conduits, in other embodiments probe 300 includes any number of inlet and outlet conduits and any number of plenums that enable operation of gas temperature measurement system 102 and temperature measurement probe 300 as described herein. Also, in some embodiments, where cooling is not necessary, alternative embodiments of probe 300 include no heat removal features.

In the exemplary embodiment, probe 300 is substantially stationary. Alternatively, probe 300 is coupled to at least one translation device (shown in FIG. 5) through outer casing 302 such that high-temperature thermocouple 310, gas emissions sampling apertures 314, and thin filament 316 are translated in one, two, or three dimensions to facilitate movement around hot gas path 220 (shown in FIG. 2) to get a map of the gas temperatures and species constituents in several planes. In some embodiments, the translation devices include stepper motors coupled to a feedthrough portion of probe 300. Each stepper motor provides translation in only one direction. Therefore, translation of probe 300 in two or three dimensions requires two and three stepper motors, respectively. Many known stepper motors are sufficiently rugged to operate in the high-temperature environments of hot gas path 220. In addition, in some embodiments, heat removal systems associated with the translating mechanisms further facilitate life extension of such translating mechanisms.

Figure 4:
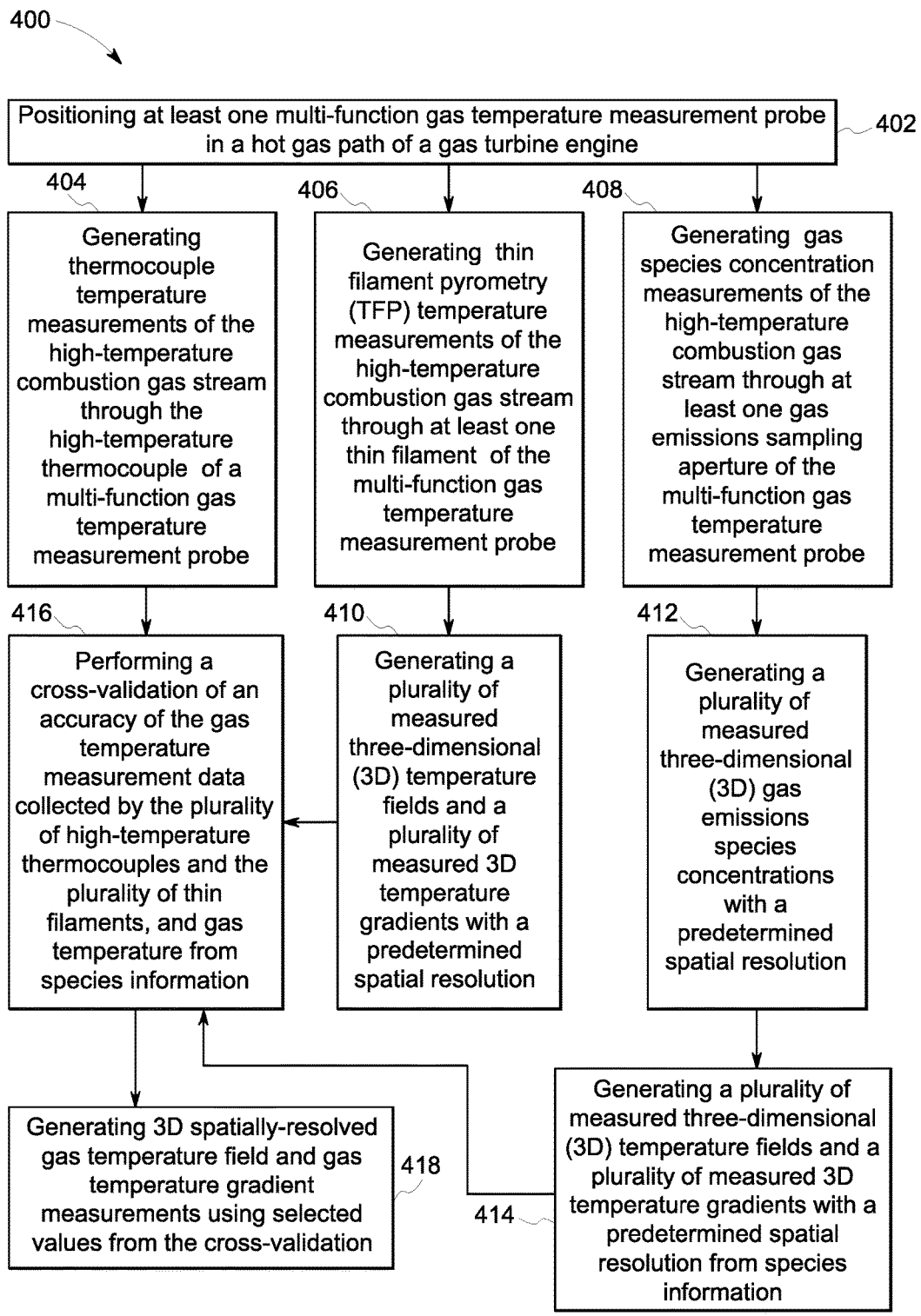
FIG. 4 is a flow chart of an exemplary method of testing at least a portion of the turbomachine shown in FIGS. 1 and 2 using the temperature measurement system shown in FIG. 1 and the temperature measurement probes shown in FIG. 3.

FIG. 4 is a flow chart of an exemplary method 400 of testing at least a portion of gas turbine engine system 101 shown in FIGS. 1 and 2 using temperature measurement system 102 (shown in FIG. 1) and temperature measurement probe 300 (shown in FIG. 3). In the exemplary embodiment, the steps of method 400 are performed substantially continuously. Alternatively, the steps of method 400 are executed at predetermined intervals.

Referring to FIGS. 1-3 with FIG. 4, method 400 includes positioning 402 at least one multi-function gas temperature measurement probe, i.e., one or more of probes 300 in a flow path, i.e., hot gas path 220 of a fluid, i.e., a high temperature gas stream (not shown). Method step 402 is performed through manually positioning probes 300 in hot gas path 220 for taking measurement data in one dimension only or using translation devices to move probes 300 within hot gas path 220 for taking measurement data in two or three dimensions.

Method 400 further includes generating 404 thermocouple temperature measurements of the high-temperature combustion gas stream through high-temperature thermocouple 310 of multi-function gas temperature measurement probe 300. Method 400 also includes generating 406 thin filament pyrometry (TFP) temperature measurements of the high-temperature combustion gas stream through at least one thin filament 316 of multi-function gas temperature measurement probe 300. Method 400 further includes generating 408 gas species concentration measurements of the high-temperature combustion gas stream through a plurality of gas emissions sampling apertures 314 of multi-function gas temperature measurement probe 300, where high-temperature thermocouple 310, thin filament 316, and gas emissions sampling apertures 314 are proximate to each other. In the exemplary embodiment, method steps 404, 406, and 408 are performed substantially simultaneously through their respective systems, i.e., TC electronics system 150, optical system 124, and gas analyzer system 140, respectively. Alternatively, method steps 404, 406, and 408 are performed individually through their respective systems.

Method 400 also includes generating 410 a plurality of measured three-dimensional (3D) temperature fields and a plurality of measured 3D temperature gradients with a predetermined spatial resolution using the TFP temperature measurements. Method 400 further includes generating 412 a plurality of measured 3D gas emissions species concentrations with a predetermined spatial resolution with the gas species concentration measurements. Method 400 also includes generating 414 a plurality of measured 3D temperature fields and a plurality of measured 3D temperature gradients with a predetermined spatial resolution from the measured 3D gas emissions species concentration information. The species information is used to compute approximate gas temperatures through known chemistry relationships within the combustion gases.

Method 400 also includes performing 416 a cross-validation of an accuracy of the gas temperature measurement data collected by the plurality of high-temperature thermocouples 310, the plurality of thin filaments 316, and the computed gas temperature data derived from the species information. Such cross-validation is a check, or verification of the remaining temperature data after a temperature data reduction is completed, with the TFP and gas species data having a greater likelihood of inaccuracy and removal from the data to be validated. Method 400 further includes generating 418 3D spatially-resolved gas temperature field measurements and gas temperature gradient measurements using selected values from the cross-validation of the accuracy of the gas temperature measurement data collected by the plurality of high-temperature thermocouples and the plurality of thin filaments and the gas temperature data generated from the measured 3D gas emissions species concentrations. Such selected values will primarily be based on the determination of the accuracy such that the most accurate values are used for the 3D spatially-resolved gas temperature field measurements and gas temperature gradient measurements.

The above-described gas temperature measurement probes and systems described herein use an integrated suite of temperature measurement devices suited for high-temperature environments. Specifically, the gas temperature measurement probes and systems described herein integrate thin filament pyrometry (TFP), high temperature thermocouples (TC), and gas emissions sampling probes into a single package that is easily inserted into the hot gas path of gas turbine engines. Also, the integrated TFP/TC/gas emissions probe is water-cooled to facilitate service life extension in the harsh environments. The TFP portion of the probe facilitates spatial resolution of the temperature fields and gradients in three dimensions and the TFP measurements are compared to the spatially resolved emissions measurements. Moreover, the probes described herein may be used in a stationary mode and they may be mounted on a translating device (or devices) and moved around the hot gas path to get a map of the gas temperatures in several planes. The probes described herein are especially suited for testing arrangements to facilitate cross-validation of the accuracy of gas temperature measurement data for product validation.

An exemplary technical effect of the methods, systems, and apparatus described herein includes at least one of: (a) substantially reduced physical intrusion into the hot gas path of gas turbine engines due to the elimination of multiple independent temperature measurement probes; (b) reduced material and installation costs; (c) increasing the accuracy and spatial resolution of the associated temperature measurements through taking temperature measurements with three devices in close proximity; and (d) facilitating cross-validation of the accuracy of gas temperature measurement data for product validation under testing conditions.

Exemplary embodiments of gas temperature measurement systems for gas turbine engines are described above in detail. The gas temperature measurement systems, and methods of operating such systems are not limited to the specific embodiments described herein, but rather, components of systems and/or steps of the methods may be utilized independently and separately from other components and/or steps described herein. For example, the methods may also be used in combination with other systems requiring observation of temperatures in high temperature environments, and are not limited to practice with only the gas turbine engines as described herein. Rather, the exemplary embodiment can be implemented and utilized in connection with many other high temperature applications.

Although specific features of various embodiments of the invention may be shown in some drawings and not in others, this is for convenience only. In accordance with the principles of the invention, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A multi-function gas temperature measurement probe comprising:
an outer casing having a face and a heat removal portion disposed along a side of the outer casing that is opposite the face of the outer casing, the heat removal portion of the outer casing having an inlet configured to receive a cooling fluid into the outer casing through the side of the outer casing and at least one outlet for directing the cooling fluid out of the outer casing through the side of the outer casing;

at least one high-temperature thermocouple inset within the face of the outer casing;

at least one gas emissions sampling aperture defined within the face of the outer casing; and at least one thin filament coupled to the outer casing such that the face of the outer casing is located between the at least one thin filament and the heat removal portion of the outer casing, wherein the at least one high-temperature thermocouple, the at least one gas emissions sampling aperture, and the at least one thin filament are proximate to each other;

wherein the multi-function gas temperature measurement probe is an integrated device that integrates the at least one thin filament, the at least one high-temperature thermocouple, and the at least one gas emissions sampling aperture into a single package inserted into a hot gas path of a gas turbine engine.

2. The measurement probe in accordance with claim 1, wherein the outer casing comprises a high-temperature alloy.

3. The measurement probe in accordance with claim 1, wherein the outer casing includes at least two of the outlets through which the cooling fluid exits the outer casing on opposite sides of the inlet into the outer casing.

4. The measurement probe in accordance with claim 1, wherein the heat removal portion of the outer casing is included in a cooling fluid shell defining at least one cooling fluid plenum therein, the at least one cooling fluid plenum coupled in flow communication with the inlet and the at least one outlet.

5. The measurement probe in accordance with claim 1, wherein the outer casing includes thin filament standoffs projecting from the face of the outer casing in a direction that is opposite the side having the heat removal portion, wherein the at least one thin filament extends from one of the thin filament standoffs to another of the thin filament standoffs.

6. The measurement probe in accordance with claim 1, further comprising:
gas emissions sampling apertures extending into the face of the outer casing, the gas emissions sampling apertures configured to facilitate measuring gas species concentrations of at least a portion of the hot gas path.

7. A gas temperature measurement system comprising:
at least one multi-function gas temperature measurement probe comprising:
an outer casing having a face and a heat removal portion disposed along a side of the outer casing that is opposite the face of the outer casing, the heat removal portion of the outer casing having an inlet configured to receive a cooling fluid into the outer casing through the side of the outer casing and at least one outlet for directing the cooling fluid out of the outer casing through the side of the outer casing;
at least one high-temperature thermocouple inset within the face of the outer casing;
at least one gas emissions sampling aperture defined within the face of the outer casing; and
at least one thin filament coupled to the outer casing such that the face of the outer casing is located between the at least one thin filament and the heat removal portion of the outer casing, wherein the at least one high-temperature thermocouple, the at least one gas emissions sampling aperture, and the at least one thin filament are proximate to each other;
an optical system configured to receive at least a portion of thermal radiation emitted from said at least one thin filament;
a thermocouple electronics system coupled to the at least one high-temperature thermocouple; and
a gas analyzer system coupled to the at least one gas emissions sampling aperture;
wherein the at least one multi-function gas temperature measurement probe is an integrated device that integrates the at least one thin filament, the at least one high-temperature thermocouple, and the at least one gas emissions sampling aperture into a single package inserted into a hot gas path of a gas turbine engine.

8. The gas temperature measurement system in accordance with claim 7, further comprising:
a controller communicatively coupled to the optical system, the thermocouple electronics system, and the gas analyzer system, the controller configured to:
transform optical system electrical signals to thin filament pyrometry temperature indications;
transform thermocouple electronics system electrical signals to thermocouple temperature indications; and
transform gas analyzer system electrical signals to gas species concentration indications.

9. The gas temperature measurement system in accordance with claim 7, further comprising:
a plurality of multi-function gas temperature measurement probes including:
a plurality of the high-temperature thermocouples;
a plurality of the gas emissions sampling apertures; and
a plurality of the thin filaments, the plurality of multi-function gas temperature measurement probes configured to facilitate at least one of:
spatial resolution of temperature fields and temperature gradients measured in three dimensions by the plurality of thin filaments;
spatial resolution of gas emissions species concentrations measured in the three dimensions by the plurality of gas emissions sampling apertures;
spatial resolution of the temperature fields and the temperature gradients generated in the three dimensions based on the spatial resolution of the gas emissions species concentrations;
cross-validation of an accuracy of gas temperature measurement data collected by the plurality of high-temperature thermocouples and the plurality of thin filaments; or
generation of spatially-resolved gas temperature field measurements and gas temperature gradient measurements using selected values from the cross-validation of the accuracy of the gas temperature measurement data.

10. The gas temperature measurement system in accordance with claim 7, wherein the outer casing comprises a high-temperature alloy.

11. The gas temperature measurement system in accordance with claim 7, wherein the outer casing includes at least two of the outlets through which the cooling fluid exits the outer casing on opposite sides of the inlet into the outer casing.

12. The gas temperature measurement system in accordance with claim 11, wherein the heat removal portion of the outer casing is included in a cooling fluid shell defining at least one cooling fluid plenum therein, the at least one cooling fluid plenum coupled in flow communication with the inlet and the at least one outlet.

13. The gas temperature measurement system in accordance with claim 7, wherein the outer casing includes thin filament standoffs projecting from the face of the outer casing in a direction that is opposite the side having the heat removal portion, wherein the at least one thin filament extends from one of the thin filament standoffs to another of the thin filament standoffs.

14. A method of testing at least a portion of a gas turbine engine, the method comprising:
generating thermocouple temperature measurements of a high-temperature combustion gas stream through at least one high-temperature thermocouple disposed within a face of an outer casing of a multi-function gas temperature measurement probe that also includes a heat removal portion on a side of the outer casing that is opposite the face of the outer casing;
generating thin filament pyrometry (TFP) temperature measurements of the high-temperature
combustion gas stream through at least one thin filament coupled with the outer casing of the multi-function gas temperature measurement probe such that the face of the outer casing is between the at least one thin filament and the heat removal portion of the outer casing;
generating gas species concentration measurements of the high-temperature combustion gas stream through at least one gas emissions sampling aperture in the face of the multi-function gas temperature measurement probe, wherein the at least one high-temperature thermocouple, the at least one thin filament, and the at least one gas emissions sampling aperture are proximate to each other; and
cooling the multi-function gas temperature probe by directing a cooling fluid into an inlet in the heat removal portion of the multi-function gas temperature probe that is opposite of the face of the multi-function gas temperature probe,
wherein the multi-function gas temperature measurement probe is an integrated device that integrates the at least one thin filament, the at least one high-temperature thermocouple, and the at least one gas emissions sampling aperture into a single package inserted into a hot gas path of the gas turbine engine.

15. The method in accordance with claim 14, wherein the TFP temperature measurements include a plurality of measured three-dimensional (3D) temperature fields and a plurality of measured 3D temperature gradients with a predetermined spatial resolution.

16. The method in accordance with claim 14, wherein the gas species concentration measurements include a plurality of measured three-dimensional (3D) gas emissions species concentrations with a predetermined spatial resolution.

17. The method in accordance with claim 16, further comprising:
generating a plurality of measured 3D temperature fields and a plurality of measured 3D temperature gradients with a predetermined spatial resolution from the measured 3D gas emissions species concentrations.

18. The method in accordance with claim 17, wherein generating the thermocouple the temperature measurements and generating the TFP temperature measurements through the multi-function gas temperature measurement probe comprises performing a cross-validation of an accuracy of the gas temperature measurement data collected by the plurality of high-temperature thermocouples and the plurality of thin filaments.

19. The method in accordance with claim 18, further comprising:
generating 3D spatially-resolved gas temperature field measurements and gas temperature gradient measurements using selected values from the cross-validation of the accuracy of the gas temperature measurement data collected by the at least one high-temperature thermocouple and the at least one thin filament and the gas temperature data generated from the measured 3D gas emissions species concentrations.

20. The method in accordance with claim 14, further comprising:
positioning the multi-function gas temperature measurement probe in the hot gas path.

* * * * *